United States Patent
Stark

(10) Patent No.: US 6,521,893 B2
(45) Date of Patent: Feb. 18, 2003

(54) METHOD AND APPARATUS FOR IMPROVING IMAGE QUALITY IN POSITRON EMISSION TOMOGRAPHY

(75) Inventor: Iain Stark, Manotick (CA)

(73) Assignee: IS2 Research Inc., Nepean (CA)

( * ) Notice: Subject to any disclaimer, the term of this patent is extended or adjusted under 35 U.S.C. 154(b) by 0 days.

(21) Appl. No.: 09/759,523

(22) Filed: Jan. 16, 2001

(65) Prior Publication Data

US 2001/0017352 A1 Aug. 30, 2001

Related U.S. Application Data

(63) Continuation-in-part of application No. 09/127,987, filed on Aug. 3, 1998.

(30) Foreign Application Priority Data

Aug. 1, 1997 (CA) .............................................. 2212196

(51) Int. Cl.$^7$ ................................................ G01T 1/20
(52) U.S. Cl. ..................... 250/369; 250/252.1
(58) Field of Search .......................... 250/369, 252.1, 250/363.02, 363.03, 363.04, 363.07, 363.09, 363.01; 378/4

(56) References Cited

U.S. PATENT DOCUMENTS

| 5,646,408 | A | * | 7/1997 | Goldberg et al. | ...... | 250/363.07 |
|---|---|---|---|---|---|---|
| 5,751,000 | A | * | 5/1998 | McCroskey et al. | ... | 250/363.03 |
| 5,841,140 | A | * | 11/1998 | McCroskey et al. | ... | 250/363.03 |
| 6,072,177 | A | * | 6/2000 | McCroskey et al. | ..... | 250/252.1 |
| 6,175,119 | B1 | * | 1/2001 | Stark | .......................... | 250/369 |
| 6,346,706 | B1 | * | 2/2002 | Rogers et al. | ......... | 250/363.04 |

* cited by examiner

Primary Examiner—Constantine Hannaher
Assistant Examiner—Otilia Gabor
(74) Attorney, Agent, or Firm—Finnegan, Henderson, Farabow, Garrett & Dunner, L.L.P.

(57) ABSTRACT

A method and apparatus for improving the image quality of positron emission tomography is disclosed. This is achieved by analyzing individual photomultiplier tubes for true events. The apparatus includes a photomultiplier tube for generating a photomultiplier tube signal. A series of pull up resistors generates a code signal identifying the photomultiplier tube. A clock generates a time stamp to the photomultiplier tube signal. A bus buffer generates an encoded signal. A position computing device calculates the position of the photomultiplier tube. An image computer generates an image from a plurality of encoded signals. A display displays the image. Analyzing data from individual photomultiplier tubes results in smaller areas and smaller amounts of data to be processed. This then permits smaller time frame windows to be used. The use of time stamps also permits data before and after an event to be recorded.

7 Claims, 5 Drawing Sheets

METHOD AND APPARATUS FOR IMPROVING IMAGE QUALITY IN POSITRON EMISSION TOMOGRAPHY

REFERENCE TO PARENT APPLICATION

This application is a Continuation-In-Part of "Photomultiplier Tube Identifier", U.S. Ser. No. 09/127,987, filed on Aug. 3, 1998, which is incorporated herein by reference.

FIELD OF THE INVENTION

The present invention relates to scintillation cameras. In particular, the invention relates to a method and apparatus for improving the quality of images produced during positron emission tomography.

BACKGROUND OF THE INVENTION

In the human body, increased metabolic activity is associated with an increase in emitted radiation. In the field of nuclear medicine, increased metabolic activity within a patient is detected using a radiation detector such as a scintillation camera.

Scintillation cameras are well known in the art, and are used for medical diagnostics. A patient ingests, inhales or is injected with a small quantity of a radioactive isotope. The radioactive isotope emits gamma rays that are detected by a scintillation medium in the scintillation camera. The scintillation medium is commonly a sodium iodide crystal, BGO or other. The scintillation medium emits a small flash or scintillation of light, in response to stimulating radiation, such as from a patient. The intensity of the scintillation of light is proportional to the energy of the stimulating photon, such as a gamma photon. Note that the relationship between the intensity of the scintillation of light and the gamma ray is not linear.

A conventional scintillation camera such as a gamma camera includes a detector which converts into electrical signals gamma rays emitted from a patient after radioisotope has been administered to the patient. The detector includes a scintillator and photomultiplier tubes. The gamma rays are directed to the scintillator which absorbs the radiation and produces, in response, a very small flash of light. An array of photodetectors, which are placed in optical communication with the scintillation crystal, converts these flashes into electrical signals which are subsequently processed. The processing enables the camera to produce an image of the distribution of the radioisotope within the patient.

Scintillation cameras are used to take four basic types of pictures: spot views, whole body views, partial whole body views, SPECT views, and whole body SPECT views.

A spot view is an image of a part of a patient. The area of the spot view is less than or equal to the size of the field of view of the gamma camera. In order to be able to achieve a full range of spot views, a gamma camera must be positionable at any location relative to a patient.

One type of whole body view is a series of spot views fitted together such that the whole body of the patient may be viewed at one time. Another type of whole body view is a continuous scan of the whole body of the patient. A partial whole body view is simply a whole body view that covers only part of the body of the patient. In order to be able to achieve a whole body view, a gamma camera must be positionable at any location relative to a patient in an automated sequence of views.

The acronym "SPECT" stands for single photon emission computerized tomography. A SPECT view is a series of slice-like images of the patient. The slice-like images are often, but not necessarily, transversely oriented with respect to the patient. Each slice-like image is made up of multiple views taken at different angles around the patient, the data from the various views being combined to form the slice-like image. In order to be able to achieve a SPECT view, a scintillation camera must be rotatable around a patient, with the direction of the detector head of the scintillation camera pointing in a series of known and precise directions such that reprojection of the data can be accurately undertaken.

A whole body SPECT view is a series of parallel slice-like transverse images of a patient. Typically, a whole body SPECT view consists of sixty four spaced apart SPECT views. A whole body SPECT view results from the simultaneous generation of whole body and SPECT image data. In order to be able to achieve a whole body SPECT view, a scintillation camera must be rotatable around a patient, with the direction of the detector head of the scintillation camera pointing in a series of known and precise directions such that reprojection of the data can be accurately undertaken.

Therefore, in order that the radiation detector be capable of achieving the above four basic views, the support structure for the radiation detector must be capable of positioning the radiation detector in any position relative to the patient. Furthermore, the support structure must be capable of moving the radiation detector relative to the patient in a controlled manner along any path.

In order to operate a scintillation camera as described above, the patient should be supported horizontally on a patient support or stretcher.

A certain design of gantry or support structure for a scintillation camera includes a frame upon which a vertically oriented annular support rotates. Extending out from the rotating support is an elongate support. The elongate generally comprises a pair of arms. The pair of arms generally extends through a corresponding pair of apertures in the rotating support. One end of the pair of arms supports the detector head on one side of the annular support. The other end of the pair of arms supports a counter balance weight. Thus, the elongate support is counterbalanced with a counterweight on the opposite side of the detector head.

With such a design of support suture for a scintillation camera, a patient must lie on a horizontally oriented patient support. The patient support must be cantilevered so that the detector head can pass underneath the patient. If the detector head must pass underneath only one end of the patient, such as the patent's head, the cantilevered portion of the patient support is not long enough to cause serious difficulties in the design of the cantilevered patient support. However, if the camera must be able to pass under the entire length of the patient, the entire patient must be supported by the cantilevered portion of the patient support. As the cantilevered portion of the patient support must be thin so as not to interfere with the generation of images by the scintillation camera, serious design difficulties are encountered.

Among the advantages associated with such as design of support structure is that a patient may be partially pass through the orifice defined by the annular support so that the pair of arms need not be as long. However, the patient support must be able to support the patient in this position relative to the annular support, must be accurately positionable relative to the annular support, and must not interfere either with the rotation of the annular support or with the cables which will inevitably extend from the detector head to a nearby computer or other user control.

The photomultiplier tubes in a scintillation camera generate electric signals. The signals are processed, and images are created corresponding to the radiation emitted by the patient.

From time to time, images are generated that contain one or more artifacts or flaws. Artifacts are often caused by one or more malfunctioning photomultiplier tubes. A malfunctioning photomultiplier tube maybe generating incorrect signals, may be generating no signal at all, or the processing of the signals from a particular photomultiplier tube may not be proper.

To determine the cause of the artifact and then correct the artifact, it is important to identify all malfunctioning photomultiplier tubes. However, inspecting and testing photomultiplier tubes is difficult, time consuming and expensive.

From time to time, images of poor quality are also generated. Of particular concern are the images produced by Position Emission Tomography. Position Emission Tomography (PET) is a practice common in the art wherein two detectors are placed with their fields of view at 180° to one another. After the patient ingests the isotope, positrons are emitted from areas where is isotope has gathered in the body. The positrons that are released from the body in opposite directions collide with electrons in the body and effectively form two gamma rays.

The gamma rays are detected by the detectors and as mentioned above are used to generate images. However, in PET, only gamma rays originating from a collision between a positron and an electron that are detected at 180° (referred to as coincidence) from one another are considered true events. Preferably only true events are used to generate images.

Unfortunately what sometime occurs is that the gamma ray will ricochet off a second electron in the body before being emitted and the angle is changed. The two gamma rays will not be detected at 180° from one another, resulting in a "random" event. Random events are really just noise signals that when used to generate an image, cause poor quality imagery. It is known in the art that an increase in area (of field of view) results in an increase in the probability of random events. Since conventional PET cameras use relatively large detectors with large fields of view and they commonly use the total data values for the entire detector head the chance of using random events to generate an image is high. As well, since data from a large field of view must be processed, the time frame window during which data is analysed is large resulting in yet a higher probability of detecting random events.

In Constant Fraction Discrimination (CFDs) cameras, the probability of random events is also relatively high resulting in poorer quality images. FIG. 1 illustrates the data obtained from a Constant Fraction Discriminator. Constant Fraction Discriminators use a constant fraction (or percentage) of the input pulse to precisely determine the timing of an event. Inaccuracies occur when two events are detected in such a short time frame such as to create overlap. In the data when two or more events overlay, it is impossible to separate them to obtain before an event in order to separate the data as seen in FIG. 1, the data from areas A, B and C can be separated in order to analyse the individual events 1 and 2.

SUMMARY OF THE INVENTION

An object of the invention is to provide a method and apparatus for improving a PET image quality. This is achieved by analysing individual photomultiplier tubes for true events and by providing time stamps to photomultiplier tube signals. Analysing data from individual photomultiplier tubes as opposed to entire detector field of views results in smaller areas and smaller amounts of data to be processed. This then permits smaller time frame windows to be used.

The use of time stamps also permits data before and after a particular event to be kept as record.

In a positron emission tomography (PET) study using a scintillation detector wherein the scintillation detector has a scintillation crystal and a plurality of photomultiplier tubes and a pair of coincident gamma events due to an annihilation of a position are detected by the scintillation detector in order to locate the positron emission, a method for identifying the coincident gamma events is provided according to one aspect of the present invention. The method comprises the steps of: (a) receiving a photomultiplier tube signal from the photomultiplier tube when a gamma event occurs; (b) digitising the photomultiplier tube signal; (c) generating a clock signal providing a time stamp for the photomultiplier tube signal; and (d) generating an encoded signal using the digitised photomultiplier tube signal and the clock signal, the encoded signal comprising an encoded photomultiplier tube signal followed by an encoded time stamp; wherein, in a subsequent event-positioning process, photomultiplier tube signals caused by coincident gamma events are indentified by means of the encoded time stamp and the identified encoded signals are utilized for positioning of the gamma events.

In a positron emission tomography (PET) scanner using a scintillation detector wherein the scintillation detector has a scintillation crystal and a plurality of photomultiplier tubes and a pair of coincident gamma events due to an annihilation of a position are detected by the scintillation detector in order to locate the positron emission, an apparatus for identifying the coincident gamma events is provided according to another aspect of the invention. The apparatus comprises: (a) a photomultiplier tube for generating a photomultiplier tube signal when a gamma event occurs; (b) an analog-to-digital converter for digitising the photomultiplier tube signal;(c) a clock for generating a clock signal providing a time stamp for the photomultiplier tube signal; and (d) means for generating an encoded signal using the digitised photomultiplier tube signal and the clock signal, the encoded signal comprising an encoded photomultiplier tube signal followed by an encoded time stamp; wherein, in a subsequent event-positioning process, photomultiplier tube signals caused by coincident gamma events are identified by means of the encoded time stamp and the identified encoded signals are utilized for positioning the gamma events.

In a positron emission tomography (PET) scanner using a scintillation detector wherein the scintillation detector has a scintillation crystal and a plurality of photomultiplier tubes and a pair of coincident gamma events due to an annihilation of a position are detected by the scintillation detector in order to locate the positron emission, an apparatus for improving the image is provided according to another aspect of the invention. The apparatus comprises: (a) means for generating a photomultiplier tube signal after an event; (b) means for generating a code signal identifying the photomultiplier tube; (c) means for generating a clock signal providing a time stamp for the photomultiplier tube signal; (d) means for generating an encoded signal comprising the photomultiplier tube signal followed by the code signal and the time stamp; (e) means for determining whether the encoded signal has been caused by a true event; and (e) means for calculating the position of the event using the determined encoded signal.

Other advantages, objects and features of the present invention will be readily apparent to those skilled in the art from a review of the following detailed description of preferred embodiments in conjunction with the accompanying drawings and claims.

BRIEF DESCRIPTION OF THE DRAWINGS

The embodiments of the invention will now be described with reference to the accompanying drawings, in which.

Similar references are used in different figures to denote similar components.

DETAILED DESCRIPTION OF THE INVENTION

Figure 1:
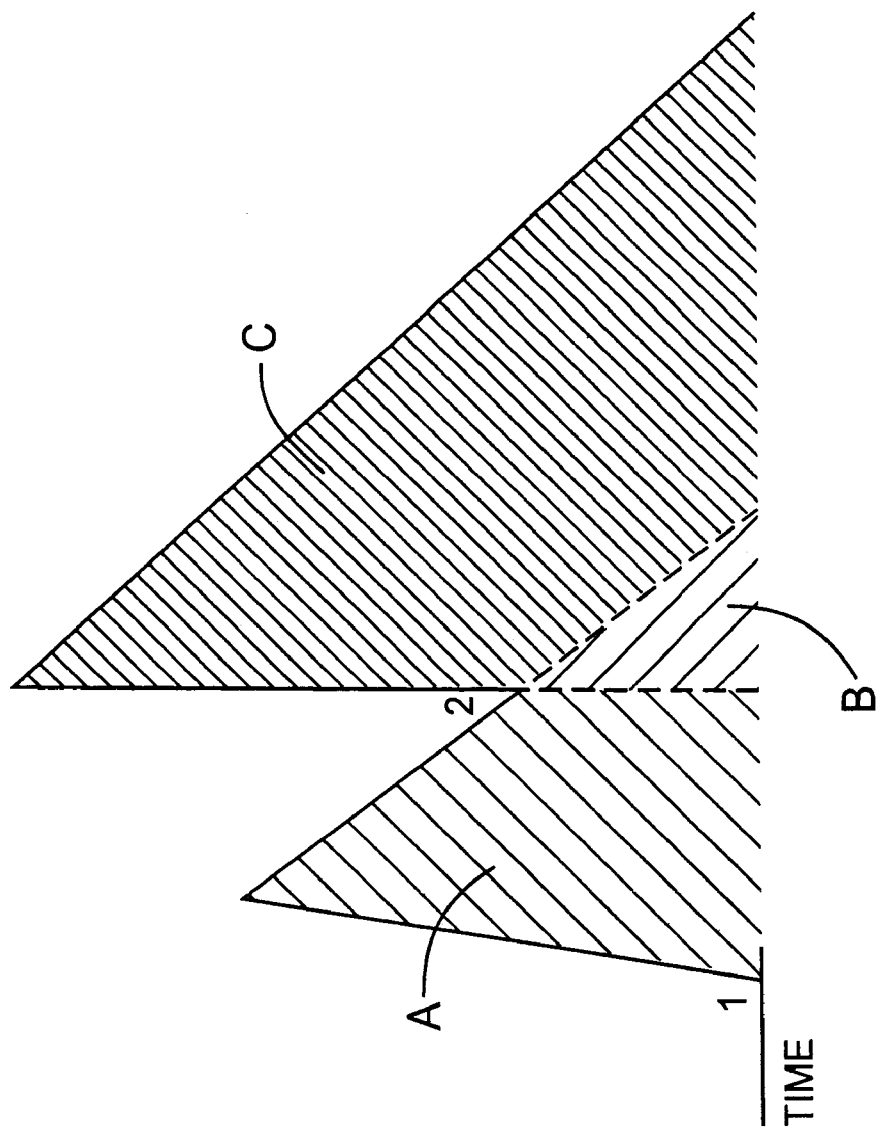
FIG. 1 illustrates the data obtained with a CFD.
Figure 2:
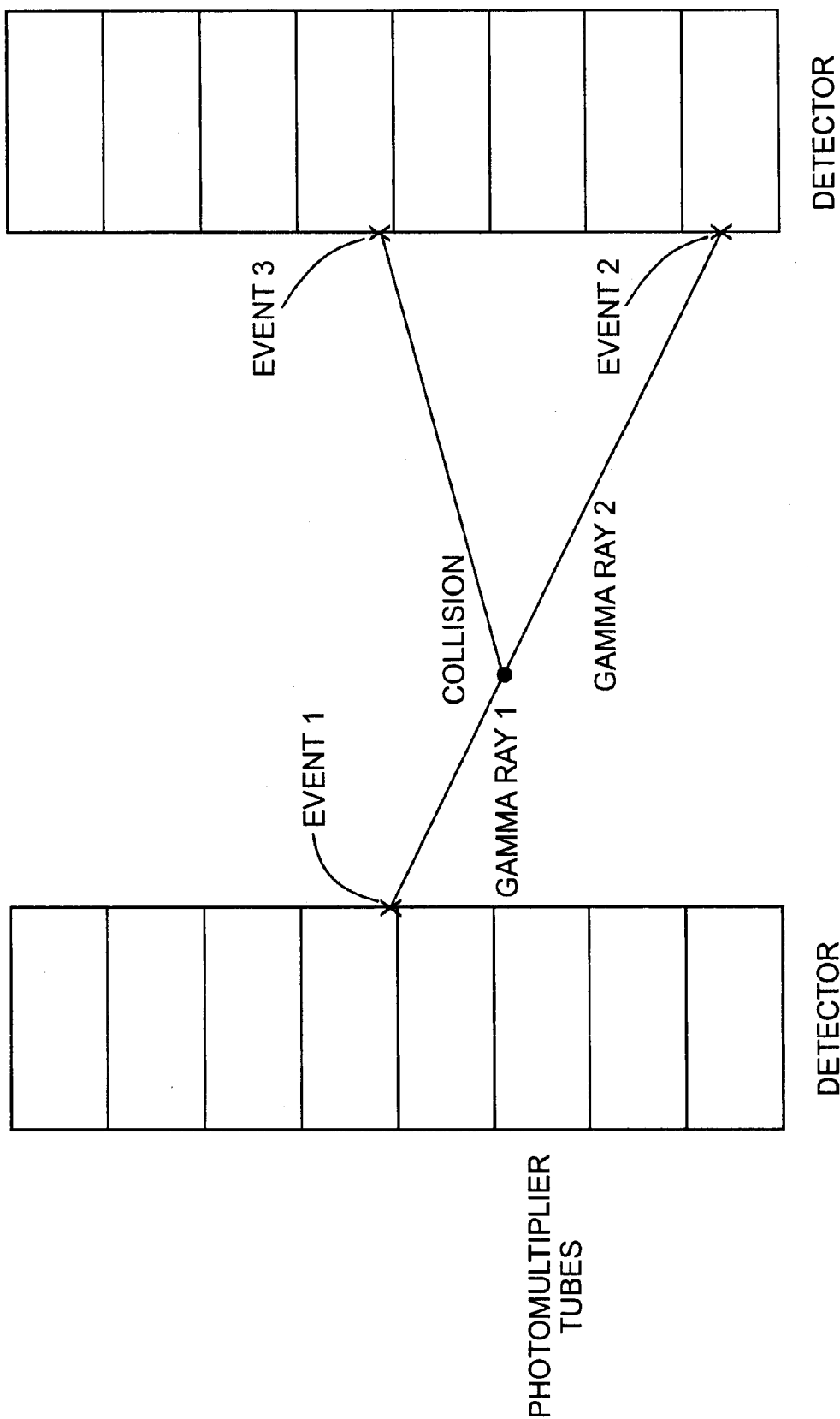
FIG. 2 illustrates the basics of PET.

FIG. 2 illustrates the basics of PET. Briefly, when a collision occurs in the body, two gamma rays are emitted and detected by the detector known as events). If it is determined that the events are true events (as detailed below), they are used in image generation. However, if one gamma ray, for example gamma ray 2, ricochets to create event 3 rather than true event 2, it causes a random or scattered event and is preferably not used in image generation.

Figure 3:
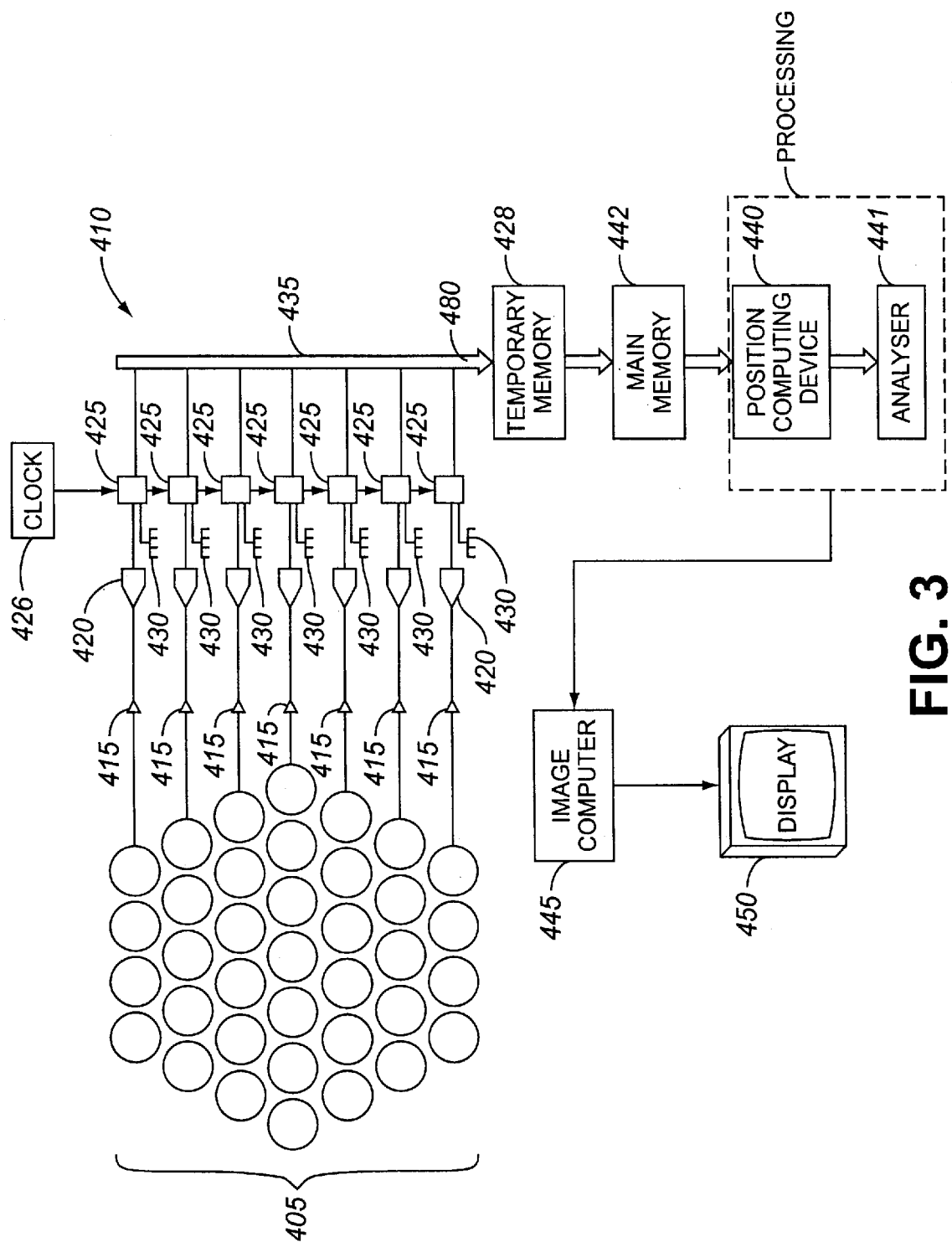
FIG. 3 is a drawing of an embodiment of the photomultiplier tube identifier of the present invention.
Figure 4:
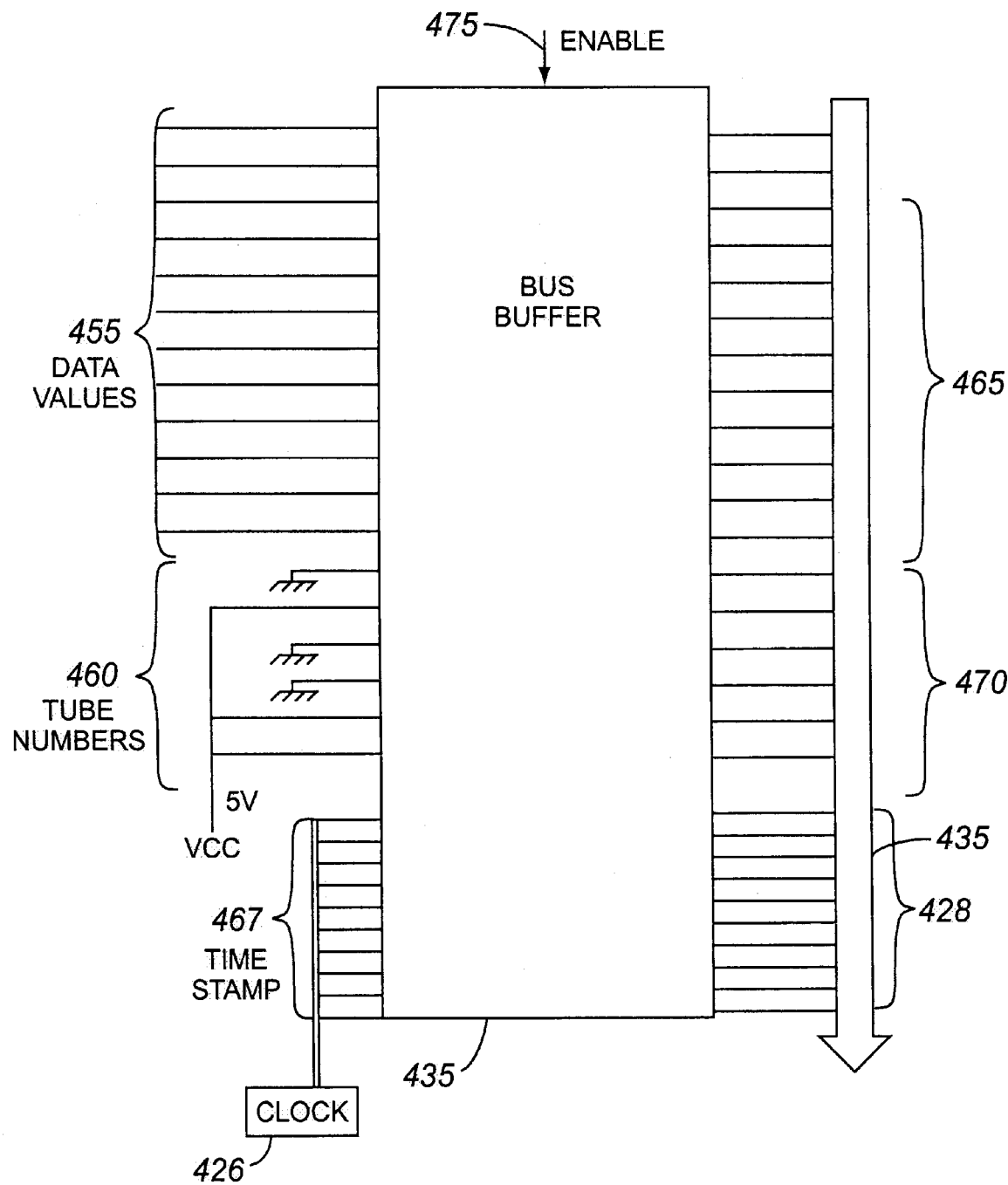
FIG. 4 is a drawing of the bus buffer of the embodiment of FIG. 3.

FIGS. 3 and 4 illustrate an array of photomultiplier tubes 405 in a scintillation camera. A photomultiplier tube identifier 410 is an apparatus for identifying a photomultiplier tube in the array of photomultiplier tubes 405.

The photomultiplier tube identifier 410 includes amplifier/integrators 415, analog to digital converters (ADCS) 420, bus buffers 425, pull-up resistors 430, a bus 435, a position computing device 440, an image computer 445, a user display 450 and a clock 426.

Output signals from individual photomultiplier tubes in the array of photomultiplier tubes 405 are amplified and integrated by the amplifier/integrators 415. The output signals from the amplifier/integrators 415 are then digitized in the analog to digital converters 420. The output signal from a digital to analog converter 420 corresponds to the strength of the signal from an individual photomultiplier tube in the array of photomultiplier tubes 405.

The bus buffers 425 receive output signals from the digital to analog converters 420. Some of the gates of the bus buffers 425 are also connected to the pull up resistors 430. The gates of the bus buffer are set by the pull up resistors 430 to a logic high or logic low which correspond to the identities of the individual photomultiplier tubes from which signals have been obtained. To each output signal from the digital to analog converters 420, the bus buffers 425 add a code below the least significant bits identifying the photomultiplier tube from which the signal was obtained. Thus, the output signals from the bus buffers 425 corresponds to the strength of the signals received from the array of photomultiplier tubes 405 plus a code identifying the photomultiplier tube from which the signals were obtained.

In addition, the clock 426 provides clock signals providing a continuously running clock or stream of time stamps to each photomultiplier tube identifier. The clock signals provide the time stamp for each photomultiplier tube output signal at a predetermined clock increment. The stream of time stamps maintain records of when events have taken place.

In a preferred embodiment, the clock increments in cycles from 0 to 256. That is, each cycle produces 256 time stamps, but any suitable number could be used depending upon the accuracy required.

In a preferred embodiment, time stamps are generated every two nanoseconds, but another suitable length of time can be chosen.

FIG. 4 illustrates a bit bus buffer 425. Output signals 455 from a digital to analog converter 420, in this case twelve most significant bits of signal data, are received by the bus buffer 425. The twelve bit output signs 455 correspond to the specific photomultiplier tube providing the output signal. Logic values 460 from pull up resistors 430, in this case 6 bits of data, provide a hard wired code corresponding to the identity of the specific photomultiplier tube. In this case, as the pull up resistors provide six bits of data, the signals from sixty four different photomultiplier tubes 405 may be encoded. As well, approximately ten bits of clock signals 461, are also written into the bus buffer and encoded. While ten bits of time stamp data is preferable, any number of bits could be used.

Upon receipt of the enable command at 475, the data (the data signal values, the photomultiplier tube identifier and time stamps) from the bus buffer is read onto the bus 435. The signal values 465, that is, the first twelve bits of data correspond to the output signal received from the digital to analog converter 415. The code values 470, that is, the next four bits of data, provide the code identifying the specific photomultiplier tube 405 providing the information. The time stamp values 428 provides the time data from the clock signals 461. The signals 460 in FIG. 4 provide a code of 010011, ground being represented by 0 and VCC being represented by 1. If more codes are required, a larger bus buffer can be used, such as a twenty or thirty two bit bus buffer.

The first twelve bits of each encoded signal 480 are the signals values 465, and six bits of each encoded signal 480 are the code values 470 while the remaining bits are the time stamp values 428. The encoded signals 480 are received by a processing unit. Since the code values 470 are in the low part of the encoded signal 480 or data word used by the position computing device 440, the change in value created by adding the code values 470 to the signal values 470 is negligible. Therefore, the code values 470 do not need to be removed before the encoded signal 480 is used by the position computing device 440. For example, the encoded signal may represent the value 1,001,325.238. The final two digits, that is, eight and three, may be the code identifying the thirty eighth photomultiplier tube in the array. The 0.038 value and the time stamp data could be removed from the encoded signal 480 prior to processing by the position computing device 440 and reattached to the signal 480 afterwards. However, such a calculation would not be beneficial as the 0.038 a negligible value compared with the value 1,001,325.238. If an artifact appears on the generated image, and the artifact can be traced to the data value 1,001,325.238, then photomultiplier tube number thirty eight can be repaired or replaced. Similarly, if an artifact appears on the generated image, and fewer data values traceable to photomultiplier tube number thirty eight than are statistically expected, then photomultiplier tube number thirty eight may need repairing or replacing.

Encoded signals 480, including the time stamp, are read onto the bus buffer 425. This data for each multiplier tube is then fed across the bus 435 and may be stored in a temporary memory 428. The data coming from a particular photomultiplier tube can be analysed by a data analyser 441. If there is an event, the data before that event, and after the event is recorded. In the case of CFOs, this allows overlapping event signals to be separated into individual true event signals. In other words, if data from two events have overlapped, the data values for one event can be subtracted or removed from the data values for the second event. This is known in the art as deconvalving the events.

Figure 5:
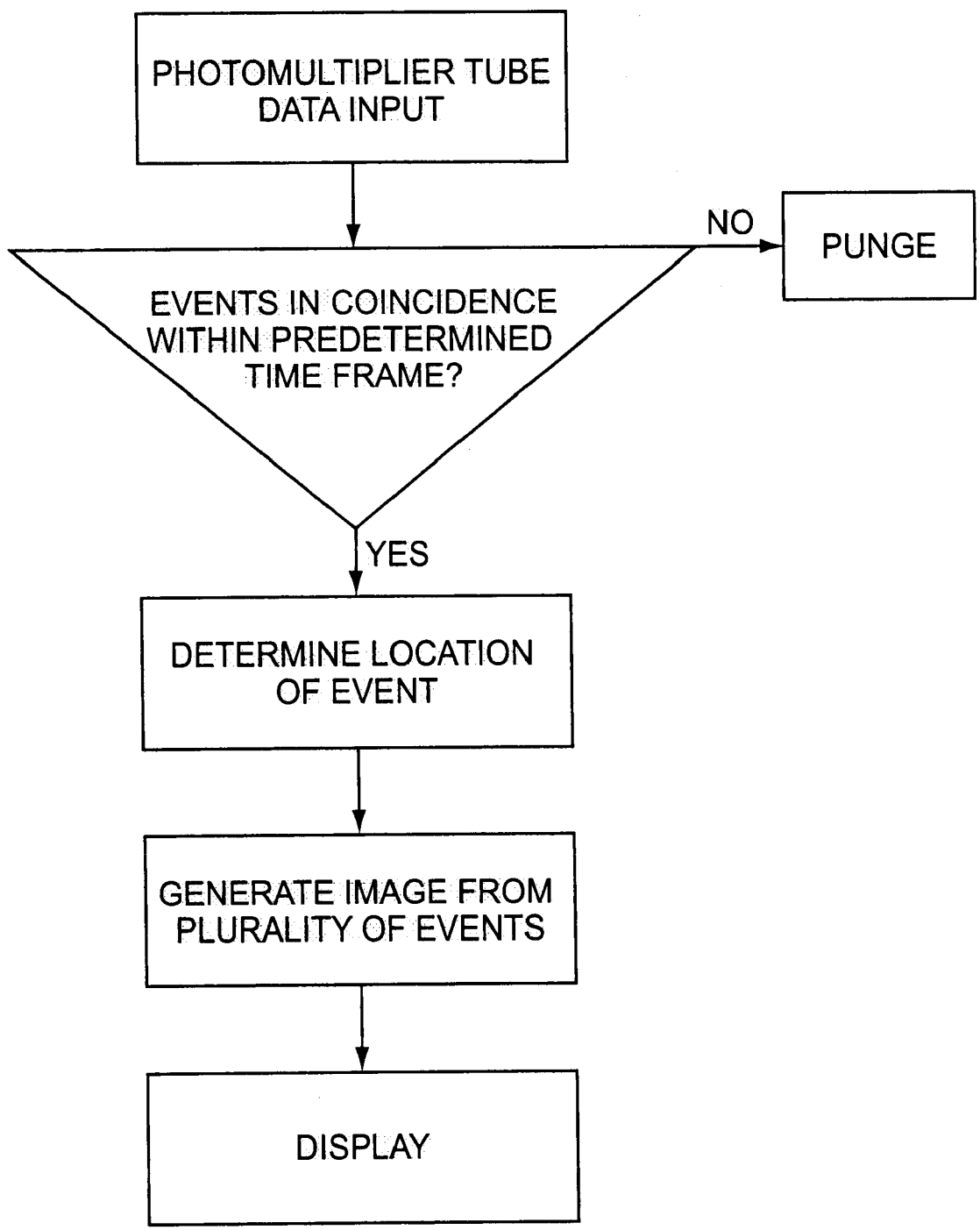
FIG. 5 is a flowchart illustrating the operation of the data analyser.

Similarly, the signals for all the photomultiplier tube outputs cam be analysed for photomultiplier tubes that are at 180° degrees to one another. From this data, it can be determined whether an event is within a certain time window, and whether those photomultiplier tubes are in coincidence. This is accomplished by analysing the data for two photomultiplier tubes at 180° degrees within a very small time window, for example, two nanoseconds. The true events data is then transferred to a main memory 442 and then to processing and image generation. The other data (random data) is effectively useless and may be purged. In this way, the position computing device 440 can transmit information to the image computer 445 and then the display 450 quickly and inexpensively while retaining intact information identifying the specific photomultiplier tubes corresponding the specific data. Referring to FIG. 5, therefore, first individual tube values are analysed to determine whether an events are in coincidence and then to determine the location of the event.

Prior art systems typically operate in the following manner: when events occur, the location of the events are determined, and then whether the events are in coincidence is determined using the total data values from the entire detector heads.

As mentioned above, quality of PET imagery is affected by two factors: the probability of random events and the size of the time window.

Since the probability of random events increases as the field of view area increases, it is desirable to have less area to improve the PET images. Therefore, individual photomultiplier tubes are placed in coincidence which reduces the area, and the probability of random events is minimized. The data from individual photomultiplier tubes is used to determine coincidence as opposed to the data from the entire detector head. Note that it may be possible to have photomultiplier tubes that are skewed because it is where the events occur in the crystal that determine whether they are in coincidence.

Another way to improve PET images is to have smaller time windows during which data is analysed such that the time to pick up random events is reduced. Encoding a time stamp to each photomultiplier tube at predetermined times produces a stream of time stamps for each tube. Then each stream can be analysed to determined which tubes are in coincidence. Tubes in coincidence will have the same time stamp, or match a time stamp within a predetermined time window. By analysing individual photomultiplier tube data, smaller amounts of data are processed allowing a smaller time window to be used.

Numerous modifications, variations and adaptations may be made to the particular embodiments of the invention described above without departing from the scope of the invention, which is defined in the claims.

I claim:

1. In a positron emission tomography (PET) scanner using a scintillation detector wherein the scintillation detector has a scintillation crystal and a plurality of photomultiplier tubes and a pair of coincident gamma events due to an annihilation of a position are detected by the scintillation detector in order to locate the positron emission, an apparatus for identifying said coincident gamma events, the apparatus comprising:

a photomultiplier tube for generating a photomultiplier tube signal when a gamma event occurs;

an analog-to-digital converter for digitising the photomultiplier tube signal;

a clock for generating a clock signal providing a time stamp for the photomultiplier tube signal; and means for generating an encoded signal using the digitised photomultiplier tube signal and the clock signal, the encoded signal using the digitised photomultiplier tube signal and the clock signal, the encoded signal comprising an encoded photomultiplier tube signal followed by an encoded time stamp; wherein, in a subsequent event positioning process, photomultiplier tube signals caused by coincident gamma events are identified by means of the encoded time stamp and the identified encoded signals are utilized for positioning the gamma events.

2. An apparatus as defined in claim 1 further comprising:

means for generating a code signal identifying the photomultiplier tube; and means for generating an encoded signal using the digitised photomultiplier tube signal, the clock signal and the code signal, the encoded signal comprising an encoded photomultiplier tube signal followed by an encoded time stamp and an encoded code signal.

3. An apparatus as defined in claim 1 wherein the identified encoded signals can be utilized for positioning the gamma events without removing the encoded time stamp therefrom.

4. In a positron emission tomography (PET) study using a scintillation detector wherein the scintillation detector has a scintillation crystal and a plurality of photomultiplier tubes and a pair of coincident gamma events due to an annihilation of a position are detected by the scintillation detector in order to locate the positron emission, a method for identifying said coincident gamma events, the method comprising the steps of:

(a) receiving a photomultiplier tube signal from the photomultiplier tube when a gamma event occurs;

(b) digitising the photomultiplier tube signal;

(c) generating a clock signal providing a time stamp for the photomultiplier tube signal; and (d) generating an encoded signal using the digitised photomultiplier tube signal and the clock signal, the encoded signal comprising an encoded photomultiplier tube signal followed by an encoded time stamp; wherein, in a subsequent event-positioning process, photomultiplier tube signals caused by coincident gamma events are identified by means of the encoded time stamp and the identified encoded signals are utilized for positioning the gamma events.

5. A method as defined in claim 4 further comprising the steps of:

(e) generating an encoded signal identifying the photomultiplier tube; and (f) generating an encoded signal using the digitized photomultiplier tube signal, the clock signal and the code signal, the encoded signal comprising an encoded photomultiplier tube signal followed by an encoded time stamp and an encoded code signal.

6. A method as defined in claim 4, wherein the identified encoded signals can be utilized for positioning the gamma events without removing the encoded time stamp therefrom.

7. An apparatus for improving the image in a positron emission tomography (PET) scanner using a scintillation crystal and a plurality of photomultiplier tubes and a pair of coincident gamma events due to an annihilation of a position are detected by the scintillation detector in order to locate the positron emission, the apparatus comprising:

means for generating a photomultiplier tube signal after an event;

means for generating a code signal identifying the photomultiplier tube;

means for generating a clock signal providing a time stamp for the photomultiplier tube signal;

means for generating an encoded signal comprising the photomultiplier tube signal followed by the code signal and the time stamp;

means for determining whether the encoded signal has been caused by a true event; and means for calculating the position of the event using the determined encoded signal.

\* \* \* \* \*